United States Patent
Yoo et al.

(10) Patent No.: US 11,672,745 B1
(45) Date of Patent: Jun. 13, 2023

(54) HAIR BROWNING COMPOSITION AND HAIR BROWNING METHOD USING SAME

(71) Applicant: GACHON UNIV OF INDUSTRY-ACADEMIC COOPERATION FDN, Seongnam-si (KR)

(72) Inventors: Bong Kyu Yoo, Seongnam-si (KR); Karthikeyan Selvaraj, Incheon (KR); Dong Joo Yoo, Seongnam-si (KR)

(73) Assignee: GACHON UNIV OF INDUSTRY-ACADEMIC COOPERATION FDN, Seongnam-si (KR)

( * ) Notice: Subject to any disclaimer, the term of this patent is extended or adjusted under 35 U.S.C. 154(b) by 0 days.

(21) Appl. No.: 17/813,112

(22) Filed: Jul. 18, 2022

(30) Foreign Application Priority Data

Jan. 19, 2022 (KR) .................. 10-2022-0007794
Mar. 3, 2022 (KR) .................. 10-2022-0027377

(51) Int. Cl.
| | | |
|---|---|---|
| A61Q 5/10 | (2006.01) | |
| A61K 8/365 | (2006.01) | |
| A61K 8/24 | (2006.01) | |
| A61K 8/67 | (2006.01) | |
| A61K 8/02 | (2006.01) | |
| A61K 8/41 | (2006.01) | |
| A61Q 5/06 | (2006.01) | |
| A61K 8/04 | (2006.01) | |

(52) U.S. Cl.
CPC .............. *A61K 8/365* (2013.01); *A61K 8/022* (2013.01); *A61K 8/042* (2013.01); *A61K 8/24* (2013.01); *A61K 8/41* (2013.01); *A61K 8/67* (2013.01); *A61Q 5/065* (2013.01); *A61K 2800/43* (2013.01)

(58) Field of Classification Search
CPC ........ A61K 8/365; A61K 8/022; A61K 8/042; A61K 8/24; A61K 8/41; A61K 8/67; A61K 2800/43; A61Q 5/065
USPC ............................................. 8/405
See application file for complete search history.

(56) References Cited

FOREIGN PATENT DOCUMENTS

| | | | | |
|---|---|---|---|---|
| CN | 107837212 B | * | 6/2020 | ............... A61Q 5/00 |
| WO | WO 2006053333 A1 | * | 5/2006 | ............... A61Q 5/19 |

OTHER PUBLICATIONS

English image of the Patent No. CN107837212 B dated Jun. 12, 2020 from PE2E search.*

* cited by examiner

*Primary Examiner* — Eisa B Elhilo
(74) *Attorney, Agent, or Firm* — HoustonHogle LLP

(57) ABSTRACT

A hair browning composition is capable of browning the hair without damage to the scalp and hair due to the absence of an alkaline agent, an oxidizing agent, and an aromatic amine-based compound having an improved hair browning effect and a prolonged browning effect-lasting period. The composition includes gallic acid, magnesium ascorbyl phosphate, and tromethamine.

10 Claims, 2 Drawing Sheets

HAIR BROWNING COMPOSITION AND HAIR BROWNING METHOD USING SAME

The present application claims priority to Korean Patent Application Nos. 10-2022-0007794, filed Jan. 19, 2022, and 10-2022-0027377, filed Mar. 3, 2022, the entire contents of which are incorporated herein for all purposes by these references.

BACKGROUND OF THE INVENTION

1. Field of the Invention

The present disclosure relates to a hair browning composition and a hair browning method using the same. More particularly, the present disclosure relates to a composition having an excellent browning effect and a continuous effect thereof without toxicity by not including an oxidizing agent, an alkaline agent, an aromatic amine compound, and a method for browning hair using the same.

2. Description of the Related Art

Human hair is slowly faded or changed to white due to stress, aging, etc., and there are many cases of psychological depression as well as confidence in appearance. Accordingly, numerous hair dyes have been developed and used to maintain the original color of the hair or to make the hair appear a different color desired.

In order to change the color of the hair, the hair dye must pass through the hair cuticle and penetrate into the cortex of the hair. However, since the cuticle of the hair is a strong shell that protects the hair with a structure similar to the scales of a fish, it is very difficult for the hair dye to penetrate into the cortex.

Accordingly, commercially available hair dyes additionally contain a strong alkaline agent and an oxidizing agent.

A strong alkaline agent opens the cuticle, which is closed with a scale structure, allowing the hair dye to permeate into the cortex. Here, ammonia or mono ethanolamine is mainly used as the strong alkaline agent, and these strong alkaline agents are irritating to the scalp and surrounding skin and cause inflammation in many cases.

In addition, the oxidizing agent oxidizes the pigment precursor contained in the hair dye to develop color. Here, hydrogen peroxide is mainly used as the oxidizing agent, and this oxidizing agent damages the cuticle of the hair due to its strong oxidizing power and is irritating to the scalp and surrounding skin.

In addition, since most of the pigment precursors, which are the main components of hair dye, are aromatic amine-based compounds, there are many problems that cause allergic reactions such as urticaria depending on the human constitution.

In particular, aromatic amine-based compounds represented by phenylenediamine have many harmful effects on the human body, such as skin toxicity, reproductive toxicity, and genotoxicity, so the Ministry of Food and Drug Safety in each country classifies them as hair dye and imposes strict restrictions on their use and usage.

Accordingly, while minimizing damage to the scalp and hair, research on a composition having an excellent effect of browning hair has been widely conducted.

SUMMARY OF THE INVENTION

The objective of the present disclosure is to provide a hair browning composition capable of browning hair without damage to the scalp and hair due to the absence of an alkaline agent, an oxidizing agent, or an aromatic amine-based compound and having an improved browning effect and a prolonged browning effect-lasting period and to provide a method for browning hair using the same.

One embodiment of the present disclosure provides a hair browning composition including gallic acid, magnesium ascorbyl phosphate, tromethamine, and water.

The composition may not include an oxidizing agent or an alkaline agent.

The composition may not include an aromatic amine compound.

The composition may include 0.5% to 1.5% by weight of gallic acid, 0.1% to 15.0% by weight of magnesium ascorbyl phosphate, and 0.5% to 1.5% by weight of tromethamine based on 100% by weight of water.

The composition may further include any one or more components selected from a pH adjuster, a swelling agent, a buffer, a preservative, an antioxidant, vitamin, a pigment, and a fragrance.

The formulation of the composition for browning hair may be any one selected from the group consisting of a hair conditioner, a hair tonic, a hair cream, a hair lotion, a hair paste, a hair gel, a hair pack, a hair massage, a hair liquid, a hair spray, a hair mousse, a treatment, an aerosol mousse, an aerosol spray, a perm agent, a shampoo, a rinse, a mixed type of shampoo with rinse, a soap, a powder, and an oil.

One embodiment of the present disclosure provides a method for browning hair using the hair browning composition.

The method may include applying the composition for browning the hair to the hair and then leaving it for 1 to 30 minutes.

The hair browning composition of the present disclosure may not cause toxicity problems because it does not include an oxidizing agent and an alkaline agent.

The hair browning composition of the present disclosure may not cause toxicity problems because it does not include an aromatic amine compound.

The hair browning composition of the present disclosure can be used as included in various hair products such as a hair conditioner, a hair tonic, a hair cream, a hair lotion, a hair paste, a hair gel, a hair pack, a hair massage, a hair liquid, a hair spray, a hair mousse, a treatment, an aerosol mousse, an aerosol spray, a perm agent, a shampoo, a rinse, a mixed type of shampoo with rinse , a soap, a powder, and an oil.

The hair browning composition of the present disclosure is excellent in the hair adsorption effect, thereby improving the persistence of the browning effect.

The above and other features of the invention including various novel details of construction and combinations of parts, and other advantages, will now be more particularly described with reference to the accompanying drawings and pointed out in the claims. It will be understood that the particular method and composition embodying the invention are shown by way of illustration and not as a limitation of the invention. The principles and features of this invention may be employed in various and numerous embodiments without departing from the scope of the invention.

DESCRIPTION OF THE PREFERRED EMBODIMENTS

Figure 1:
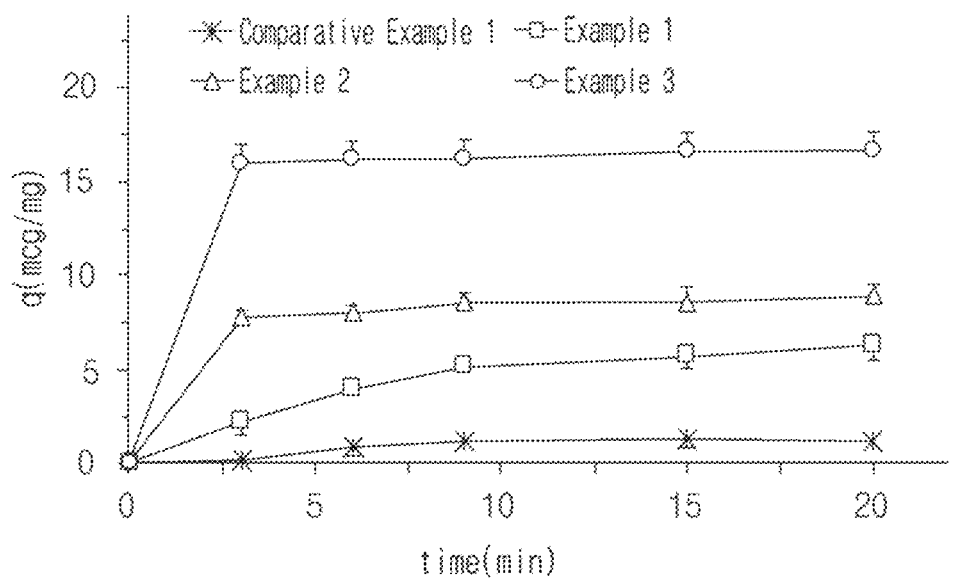
FIG. 1 is a diagram showing the amount of adsorption of gallic acid to hair.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

In general, terms and phrases used herein have their technically recognized meanings and may be learned by reference to standard texts, journal references, and literature known to those of ordinary skilled in the art. The definitions below are provided to clarify their specific use in the context of this description.

In the present specification, the term "hair" refers to hair growing on the skin of a person or an animal and, more particularly, refers to hair growing on the scalp of a person.

In the present specification, "gallic acid" is a compound having a chemical formula of $C_6H_2(OH)_3COOH$. Gallic acid is a kind of polyphenol widely present in the plant kingdom and has the characteristic of gradually changing from green to light brown in acid. Gallic acid also turns brown to reddish-brown in neutral or alkaline. However, gallic acid has a problem in that not only is the amount adsorbed to the hair very small but it is easily desorbed by detergents or the like even after adsorption.

In the present specification, "magnesium ascorbyl phosphate" refers to a compound having a chemical formula of $C_{12}H_{12}Mg_3O_{18}P_2$. Magnesium ascorbyl phosphate is known to be a stable vitamin C precursor. In the present disclosure, it serves to increase the adsorption power of gallic acid to the hair.

In the present specification, "tromethamine" is a compound having a chemical formula of $C_4H_{11}NO_3$. Tromethamine is a component mainly included in cosmetics and is used as a fragrance or pH adjuster. In the present disclosure, tromethamine is used as a component for increasing the solubility of gallic acid in water.

In the present disclosure, "browning" refers to a phenomenon that changes to brown due to oxidation, and specifically, a reactive group present in gallic acid absorbs oxygen to gradually change color to yellow, brown, dark brown, and black.

In the present disclosure, "oxidizing agent" refers to a substance that oxidizes other substances in a redox reaction and is an oxidizing agent mainly used in dyes, for example, hydrogen peroxide. The composition of the present disclosure has the effect of turning the hair brown in spite of the absence of an oxidizing agent essential for the dyeing agent.

In the present disclosure, "alkaline agent" refers to a substance for increasing the alkalinity of water, and an alkaline agent is mainly used in dyes, for example, ammonia or mono ethanolamine. The composition of the present disclosure has the effect of turning the hair brown in spite of the absence of an alkaline agent essential for the dyeing agent.

In the present disclosure, "aromatic amine compound" refers to an aromatic compound having an amino group and an aromatic amine compound mainly used in dyes, for example, phenylenediamine. The composition of the present disclosure has the effect of turning the hair brown in spite of the absence of an aromatic amine compound mainly used in the dyeing agent.

The composition is not particularly limited in formulation but maybe a composition having a formulation such as a hair conditioner, a hair tonic, a hair cream, a hair lotion, a hair paste, a hair gel, a hair pack, a hair massage, a hair liquid, a hair spray, a hair mousse, a treatment, an aerosol mousse, an aerosol spray, a perm agent, a shampoo, a rinse, a mixed type of shampoo with rinse , a soap, a powder, and an oil. The composition of each of these formulations may contain various components mixed with a general composition according to the above-described formulation or suitable for a final purpose, and the type and amount of these components may be easily selected by a person skilled in the art.

Hereinafter, the present disclosure will be described in detail through Examples, but the present disclosure is not limited by the Examples.

Example: Preparation of a Mixed Composition of Gallic Acid, Magnesium Ascorbyl Phosphate, and Tromethamine Gallic acid, magnesium ascorbyl phosphate, and tromethamine were purchased from the market and mixed in the composition shown in Table 1 below.

TABLE 1

| MAP: Magnesium ascorbyl phosphate | | | | |
|---|---|---|---|---|
| | Distilled water (g) | Gallic acid (g) | Tromethamine (g) | MAP (g) |
| Comparative Example 1 | 100 | 1.0 | 1.0 | 0 |
| Example 1 | 100 | 1.0 | 1.0 | 0.1 |
| Example 2 | 100 | 1.0 | 1.0 | 1.0 |
| Example 3 | 100 | 1.0 | 1.0 | 10.0 |

Experimental Example 1. Analysis of the Amount of Gallic Acid Adsorbed on the Hair Surface The amount of gallic acid adsorbed to the hair surface was measured by immersing the hair in the composition prepared in the Example above and analyzing the concentration of gallic acid in the composition at regular time intervals by HPLC. At this time, the concentration of gallic acid was fixed at 1.0% (w/v), and the concentration of magnesium ascorbyl phosphate was changed to 0%, 0.1%, 1.0%, and 10.0%. The adsorption amount q of gallic acid was calculated by the following formula.

$$q=\{(C_i-C_e)/m\}\times V$$

$C_i$: Gallic acid concentration in the initial state (mg/mL)
$C_e$: Gallic acid concentration in adsorption equilibrium (mg/mL)
m: Weight of hair (mg)
V Volume of test solution (mL)

HPLC analysis of gallic acid was measured with an ultraviolet detector (265 nm) using an Inertsil ODS-3 (5μm, 4.6×250 mm) column. The mobile phase was a 50:50 mixture of acetonitrile, and phosphoric acid in 1% v/v distilled water, the flow rate was 0.4 ml/min, the injection volume was 30 μl, and the column temperature was 30° C. The concentration of gallic acid was calculated using the calibration curve formula (y=203592x+3496, $R^2$=1.0000) prepared in advance for the area of the peak that appeared at the holding time of 6.8 minutes.

As a result of the experiment, it was found that the adsorption amount of gallic acid to hair was very small when magnesium ascorbyl phosphate was not added, but the adsorption amount was significantly increased when magnesium ascorbyl phosphate was added. In addition, when the concentration of magnesium ascorbyl phosphate in the solution is 0.1% w/v, it takes more than 20 minutes to reach the adsorption equilibrium, whereas when the concentration of magnesium ascorbyl phosphate is 1% w/v or more, it takes 3 minutes to reach the adsorption equilibrium. In addition, it was confirmed that the amount of gallic acid adsorbed to hair increased proportionally according to the concentration of magnesium ascorbyl phosphate, as shown in FIG. 1.

Experimental Example 2. Gray Hair Browning Effect of a Composition of Gallic Acid, Magnesium Ascorbyl Phosphate, and Tromethamine For the compositions of Examples 1 to 4, the gray hair browning effect was measured as follows. The bleached hair was put into a 10 ml capacity vial containing each composition and gently shaken. After about 3 minutes, the hair was taken out, sufficiently washed in running water, dried using a hairdryer, and then the color value ($L^*$, $a^*$, $b^*$) was measured using a color difference meter (CR-400, Konica Minolta), and the color value (E) was calculated by the following equation.

$$\text{Color value } (E) = \{(100 - L^*)^2 + (a^*)^2 + (b^*)^2\}^{1/2}$$

Figure 2:
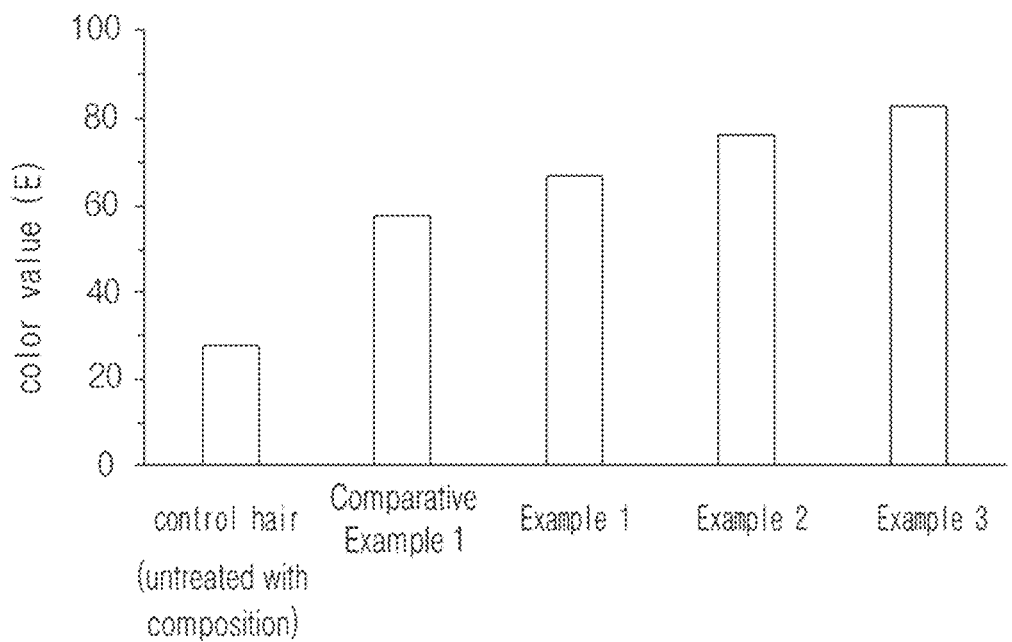
FIG. 2 is a diagram showing color values according to the amount of magnesium ascorbyl phosphate added.
Figure 3:
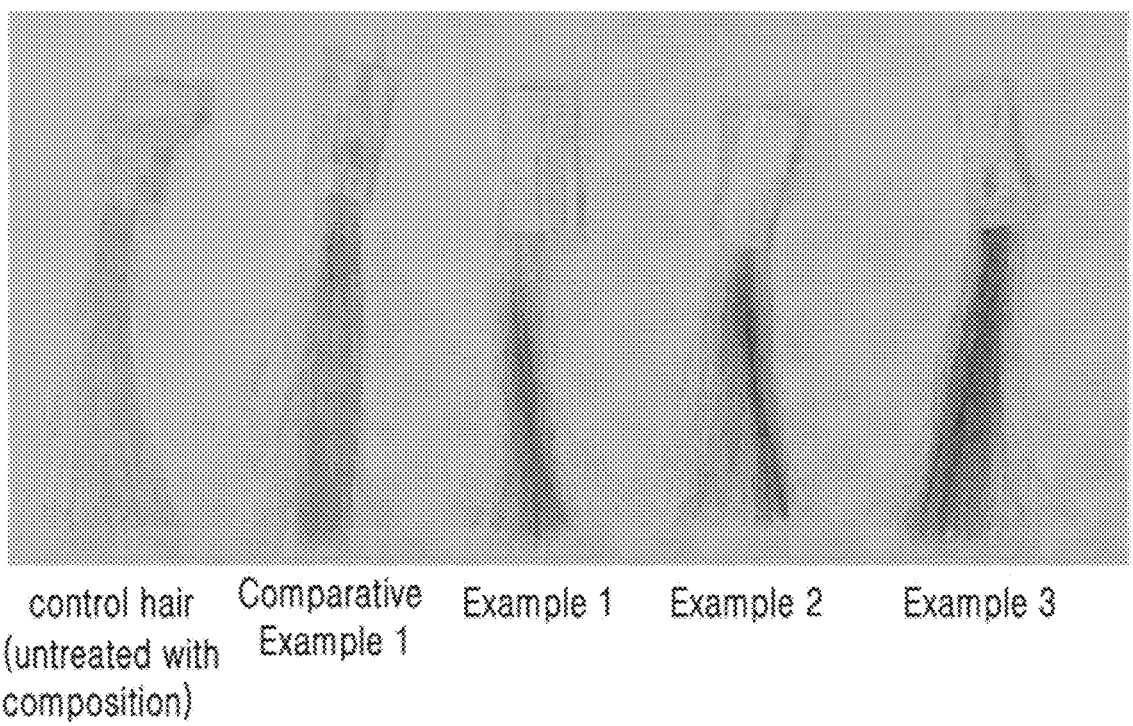
FIG. 3 is a diagram showing the effect of browning gray hair according to the amount of magnesium ascorbyl phosphate added.

As a result, it was confirmed that the browning effect of the hair was small in Comparative Example 1 in which magnesium ascorbyl phosphate was not added, whereas the browning effect of Examples 1 to 3 was significantly increased according to the amount of magnesium ascorbyl phosphate (FIGS. 2 and 3). In particular, in the case of Example 3, gallic acid was strongly adsorbed to gray hair, and it was found that there was an effect of coloring gray hair to dark brown.

Experimental Example 3. Measurement of Color Persistence

After the composition of Comparative Example 1 and the compositions of Examples 1 to 3 were applied to gray hair for 3 minutes, how long the color value lasted was measured as follows. The hair treated with each composition was immersed in distilled water containing 5% and 15% of sodium laureth sulfosuccinate and sodium C14 to C16 olefin sulfonate, respectively, and washed while rubbed for 5 minutes, then dried with a hair dryer. This process was repeated 10 times. The color value persistence according to the amount of magnesium ascorbyl phosphate added was quantitatively expressed by measuring color values ($L^*$, $a^*$, $b^*$) using a colorimeter (CR-400, Konica Minolta) after each washing.

Figure 4:
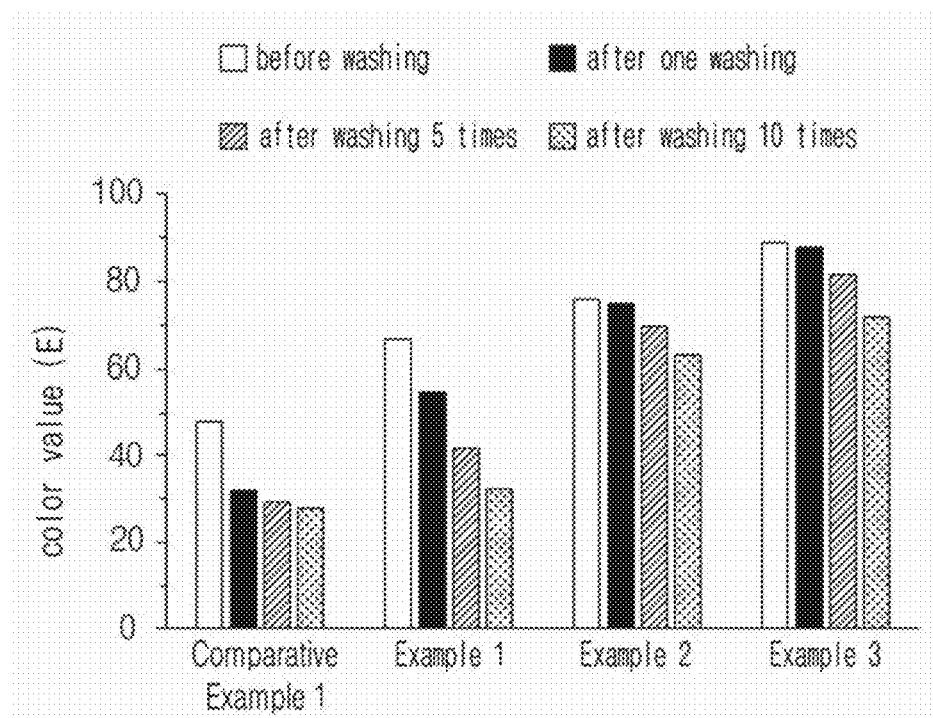
FIG. 4 is a diagram showing the color value persistence according to the amount of magnesium ascorbyl phosphate added.

As a result of the experiment, in Comparative Example 1 in which magnesium ascorbyl phosphate was not added, the browning effect almost disappeared during one washing, and the color value decreased to the same level as that of the control hair. On the other hand, in the case of the compositions of Examples 3 and 4 in which magnesium ascorbyl phosphate was added at least 1% w/v or more, there was little change in color value after one washing, and even after washing 10 times, there was no significant difference compared to before washing. The color value persistence according to the amount of magnesium ascorbyl phosphate added is shown in FIG. 4.

While this invention has been particularly shown and described with references to preferred embodiments thereof, it will be understood by those skilled in the art that various changes in form and details may be made therein without departing from the scope of the invention encompassed by the appended claims.

What is claimed is:

1. A composition for browning hair, the composition comprising:
   0.5% to 1.5% by weight of gallic acid;
   0.1% to 15.0% by weight of magnesium ascorbyl phosphate;
   0.5% to 1.5% by weight of tromethamine;
   and water based on 100% by weight of water.

2. The composition of claim 1, wherein the composition does not comprise an oxidizing agent or an alkaline agent.

3. The composition of claim 1, wherein the composition does not comprise an aromatic amine compound.

4. The composition of claim 1, wherein the composition further comprises any one or more components selected from a pH adjuster, a swelling agent, a buffer, a preservative, an antioxidant, a vitamin, a pigment, and a fragrance.

5. The composition of claim 1, wherein the formulation of the composition for browning hair is in the form of a cream, lotion, liquid, an aerosol spray, a gel, a powder, or an oil and can be used as one selected from the group consisting of a hair conditioner, a hair tonic, a hair cream, a hair lotion, a hair paste, a hair gel, a hair pack, a hair massage, a hair liquid, a hair spray, a hair mousse, a treatment, an aerosol mousse, an aerosol spray, a perm agent, a shampoo, a rinse, a mixed type of shampoo with rinse, a soap, a powder, and an oil.

6. A method for browning hair, comprising:
   applying a composition comprising 0.5% to 1.5% by weight of gallic acid, 0.1% to 15.0% by weight of magnesium ascorbyl phosphate, 0.5% to 1.5% by weight of tromethamine, and water based on 100% by weight of water to the hair of an animal; and
   washing the composition from the hair.

7. The method of claim 6, wherein the composition is applied to the hair and left for 1 to 30 minutes.

8. The method of claim 6, wherein the composition does not comprise an oxidizing agent or an alkaline agent.

9. The method of claim 6, wherein the composition does not comprise an aromatic amine compound.

10. The method of claim 6, wherein the composition further comprises any one or more components selected from a pH adjuster, a swelling agent, a buffer, a preservative, an antioxidant, a vitamin, a pigment, and a fragrance.

\* \* \* \* \*